United States Patent [19]

Puthoff et al.

[11] 4,004,463
[45] Jan. 25, 1977

[54] FLUID SAMPLING DEVICE

[75] Inventors: Carl Fredrick Puthoff, Cincinnati; James John Gardner, Hamilton, both of Ohio

[73] Assignee: Fluid Kinetics, Inc., Fairfield, Ohio

[22] Filed: Jan. 26, 1976

[21] Appl. No.: 652,468

[52] U.S. Cl. .................................. 73/425.4 R
[51] Int. Cl.² ................................ G01N 1/12
[58] Field of Search ............... 73/425.4 R, 425.6

[56] References Cited

UNITED STATES PATENTS

| | | | |
|---|---|---|---|
| 2,598,183 | 5/1952 | Long et al. | 73/425.4 |
| 3,118,307 | 1/1964 | Pettersson | 73/425.4 |

FOREIGN PATENTS OR APPLICATIONS

| | | | |
|---|---|---|---|
| 465,208 | 9/1928 | Germany | 73/425.4 |

Primary Examiner—S. Clement Swisher
Attorney, Agent, or Firm—Biebel, French & Nauman

[57] ABSTRACT

A liquid sampling device which may be lowered by a cord into a pool of fluid to sample the fluid at a particular depth includes a housing for holding a sample bottle to be filled with fluid. A remotely operable valve means prevents the sample bottle from being filled until the cord is abruptly jerked. After the bottle is filled, an automatically closing valve means seals the bottle and prevents contamination of the fluid sample by fluid at other levels as the sampling device is raised from the pool of fluid.

9 Claims, 5 Drawing Figures

U.S. Patent    Jan. 25, 1977    4,004,463
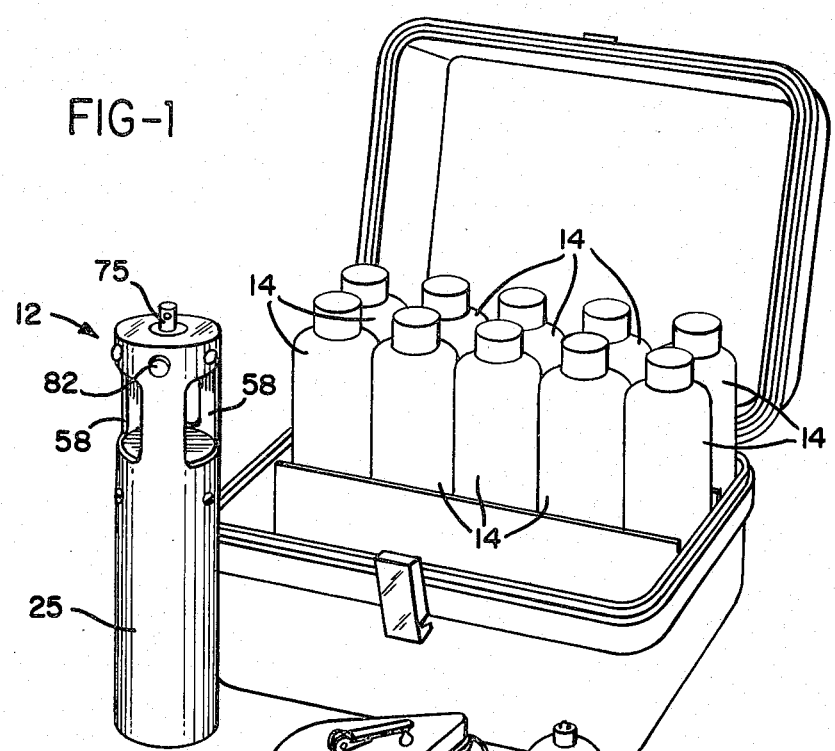
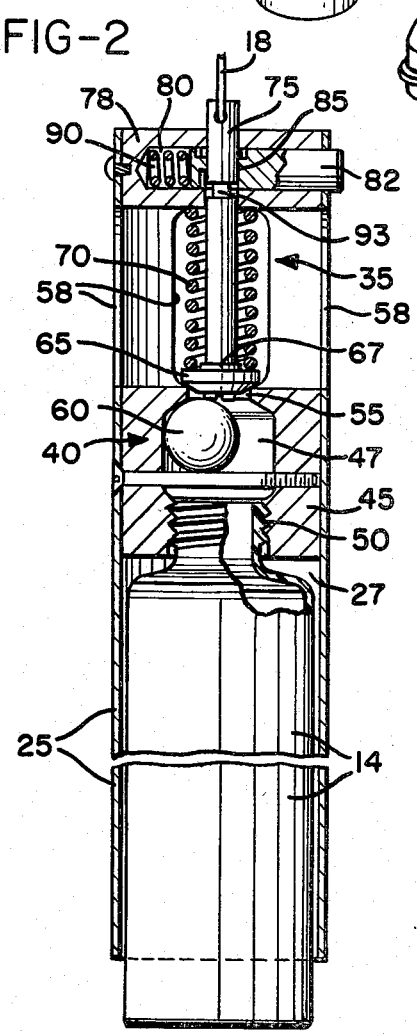
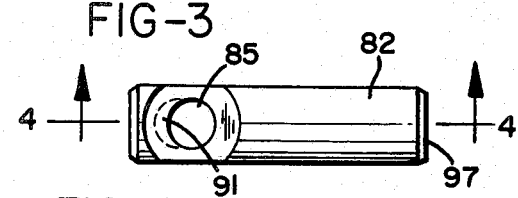
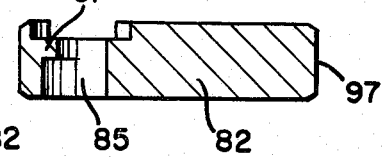
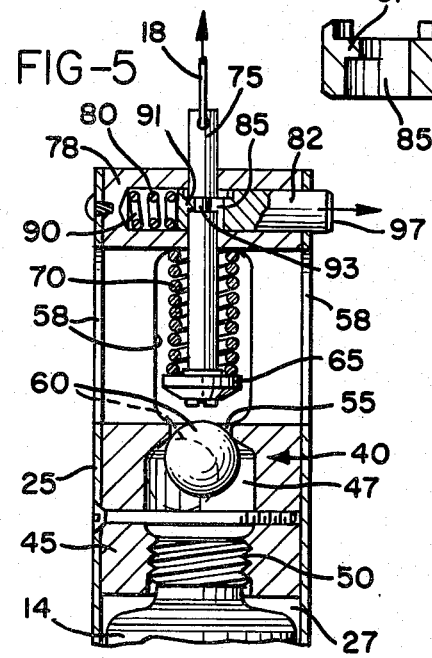

FLUID SAMPLING DEVICE

BACKGROUND OF THE INVENTION

The present invention relates to a fluid sampling device and more particularly, to a device which is to be lowered into a pool of fluid to obtain a sample quantity of the fluid at a predetermined depth below the surface of the pool.

It is often desired to obtain a set of fluid samples from a well, lake, river, or a tank with each fluid sample being taken from a different depth. A sampling device for doing this quickly will be configured to accept a detachable sampling bottle. If a chamber for receiving the fluid sample were permanently attached to the sampling device, it would be necessary to cleanse the chamber completely after taking each sample to insure that the sample would not be contaminated by residue from previously obtained samples. Such a cleansing operation would be tedious and time consuming.

A sampling device of the type to which the present invention relates must be capable of sealing the sampling bottle and maintaining this seal while the sampling device is lowered to the desired depth. Such a device should further provide for a simple method of opening the sample bottle when it is submerged to the desired depth to allow the sample bottle to fill with fluid. It is also necessary to provide a way of sealing the sample bottle after it is filled so that the fluid sample is not contaminated as the sampling device is withdrawn from the fluid.

A sampling device of the type to which the present invention relates typically is lowered into the pool by means of a cord or chain. It is possible to provide for opening and closing the sampling bottle by means of additional cords attached to the sampling device. Such complicated arrangements are, however, awkward to work with since the cords may become tangled. Additionally, such arrangements are susceptible to accidental actuation causing the sampling bottle to become filled prior to being lowered to the desired depth.

SUMMARY OF THE INVENTION

A fluid sampling device, which may be lowered by a cord into a pool of fluid to sample the fluid at a particular depth without cross contamination of the fluid sample obtained, has a housing means for holding a sample bottle to be filled with the fluid sample. A remotely operable valve means is attached to the cord and mounted on the housing means for preventing fluid from entering the bottle until the cord is abruptly jerked. An automatically closing valve means seals the bottle after it is filled with fluid and thereby prevents contamination of the fluid sample by fluid at other levels as the sampling device is raised from the pool of fluid.

The automatically closing valve means includes a means defining a chamber which communicates with the sample bottle through a first opening and with the exterior of the device through a second opening. A self-seating closure means in the chamber closes the second opening when the chamber and the bottle are filled with fluid, thus preventing contamination as the sampling device is raised. The closure means may be a hollow metal ball having a specific gravity less than that of the fluid being sampled.

The remotely operable valve has a means for blocking the second opening of the automatically closing valve and preventing fluid from entering the bottle through the chamber of the automatically closing valve until the sampling device is lowered by a cord to the appropriate level and the cord abruptly jerked. A spring means biases this means for blocking such that the second opening is normally closed. Further provided is a means for moving the means for blocking away from the second opening against the bias of the spring means and for holding the means for blocking away from the second opening after the cord is abruptly jerked. The first opening of the automatically closing valve means may be threaded for engaging the threaded neck of a sample bottle.

Accordingly, it is an object of the present invention to provide a liquid sampler device lowerable by a cord into a pool of fluid in which the sampler device takes a sample of fluid after the cord is abruptly jerked; to provide such a device in which the sample of fluid is received into an easily detachable sample bottle; to provide such a device in which the sample bottle is automatically sealed after being filled with fluid; and to provide a kit including such a sampling device and a plurality of such sample bottles.

Other objects and advantages of the present invention will be apparent from the following description, the accompanying drawings, and the appended claims.

BRIEF DESCRIPTION OF THE DRAWINGS

FIG. 1 is a perspective view showing a field kit incorporating the present invention;

FIG. 2 is a radial sectional view of the sampling device of the present invention prior to taking a sample with portions broken away and in elevation;

FIG. 3 is an elevational view of the spring pin;

FIG. 4 is a sectional view taken generally along line 4—4 in FIG. 3; and

FIG. 5 is a radial sectional view of a portion of the sampling device similar to FIG. 2 as it would appear after the sample bottle is filled.

DETAILED DESCRIPTION OF THE INVENTION

FIG. 1 shows an elevational view of a field kit which incorporates the liquid sampling device of the present invention. The sampling device 12 is fitted with one of the plastic bottles 14. The sampling device is then attached to a cord or line 17 by connector 18 and slowly lowered into the pool of fluid from which a sample is to be taken. Cord 17 may be made of Dacron or similar material or may comprise a chain or the like. Reel 20 may be used to facilitate the handling of cord 17 and bobber 22 may conveniently be attached to a line 17 at a measured distance above sampling device 12 to provide a clear indication of the depth to which the device has been lowered.

When the sampling device 12 has been lowered to the desired depth, a sharp jerk or tug on line 17 will open a valve arrangement in device 12 to permit sample bottle 14 to fill with fluid. After sample bottle 14 has completely filled, the valve arrangement in device 12 will automatically close to keep the fluid sample from becoming contaminated as the sampling device 12 is raised from the pool of fluid. The bottle 14 can then be removed from the sampling device 12 and capped for easy transportation to a laboratory. After flushing the valve arrangement in sampling device 12 with clean water, if necessary, another bottle 14 is fitted into device 12 and the sampling operation repeated at any desired level in the fluid pool.

Referring now to FIG. 2 there is shown an axial sectional view of the sampling device of the present invention with portions broken away and in elevation. The valve arrangement is shown as it would appear prior to the sampling device being lowered into the pool of fluid. An annular housing means 25 is provided for holding a sample bottle 14 to be filled with the fluid sample. Housing means 25 defines a cylindrical lower compartment 27 for holding and protecting a sample bottle. A cord attached to connector 18 is used to lower the sampling device and bottle 14 into the pool to a predetermined depth where a sample is to be taken. A remotely operable valve means 35 is attached to connector 18 and prevents fluid from entering the sample bottle 14 until the cord is abruptly jerked or tugged.

An automatically closing valve means 40 mounted in housing means 25 above lower compartment 27 includes a means 45 defining chamber 47 and is provided to seal the sample bottle 14 after the bottle is filled with fluid. This prevents contamination of the sample fluid by fluid from other levels as the sampling device is raised from the pool of fluid. Chamber 47 communicates with bottle 14 through a first opening 50 which may be threaded to engage the threaded neck of bottle 14. Chamber 47 communicates with the exterior of the sampling device through a second opening 55. As seen in FIGS. 1 and 2, housing means 25 defines a number of openings 58 which permit fluid to flow into and out of the housing. A self-seating closure means 60 in chamber 47 has a specific gravity less than that of the fluid being sampled and acts to close the second opening 55 when the bottle 14 is completely filled. A pin 59 across the lower portion of chamber 47 prevents the closure means 60, which may be a hollow metal sphere, from passing through opening 50 while allowing the sphere to move freely in the chamber.

The remotely operable valve means 35 includes a plunger means 65 for blocking the second opening 55 and for preventing fluid from entering the bottle 14 through chamber 47 prior to the time at which it is desired to take a sample. Means 65 may typically comprise a bevelled hard rubber washer backed by a flat metal washer 67. A spring means 70 is provided to bias the rubber washer 65 such that the second opening 55 normally is closed. A means for moving washer 65 away from second opening 55 against the biasing force of spring 70 includes a plunger shaft 75 which is attached to the cord by connector 18.

Portion 78 of housing 25 defines a cylindrical opening 80 transverse to shaft 75. Situated in opening 80 is pin 82 having opening 85 in which is positioned shaft 75. Spring 90 biases pin 82 transversely against shaft 75. As seen in FIGS. 3 and 4, opening 85 in pin 82 is irregularly shaped. A narrowed detent portion 91 is provided along one side of opening 85 and is dimensioned to interfit with a narrowed section 93 in shaft 75.

A comparison of FIGS. 2 and 5 illustrates the manner in which the valve arrangement of the present invention functions. As mentioned previously, the arrangement of elements shown in FIG. 2 is that of the device as it is being lowered into a pool of fluid prior to taking a sample. When the sampler device has reached the desired depth a tug on the cord attached to connector 18 will cause plunger 75 to move upwardly against the biasing force of spring 70. Pin 82, which is biased laterally by spring 90, will then engage the narrowed section 93 of plunger 75. It may thus be seen that remotely operable valve means 35 is an inertia type of valve since the inertia of the sampling device permits the valve means 35 to be actuated by an abrupt tug or jerk on the cord which also supports the sampling device.

The remotely operable valve means is then held in the position shown in FIG. 5 and fluid will enter the sample bottle 14 through the first and second openings 50 and 55, and chamber 47. Hollow metal ball 60 will assume the position shown by the dashed lines in FIG. 3 and thus will allow bottle 14 to be filled. After the bottle has been completely filled, hollow ball 60 will float upwardly and seal opening 55, as shown by the solid lines in FIG. 3.

The sampling device may then be raised without danger of contamination of the fluid sample. Bottle 14 may be removed from the sampling device and capped. An empty sample bottle is fitted into the device, remotely operable valve means 35 is reset, and the sampling device is ready to take another sample. Remotely operable valve means 35 is reset by pressing the end 97 of pin 82 such that pin 82 is disengaged from plunger 75. Spring 70 will then move plunger 75 and associated washer 65 downwardly and seal opening 55.

While the form of apparatus herein described constitutes a preferred embodiment of the invention, it is to be understood that the invention is not limited to this precise form of apparatus, and that changes may be made therein without departing from the scope of the invention.

What is claimed is:
1. A fluid sampling device, which may be lowered by a cord into a pool of fluid to sample the fluid at a particular depth without cross contamination of the fluid sample obtained, comprising:
housing means for holding a sample bottle to be filled with the fluid sample,
remotely operable valve means, attached to the cord and mounted on said housing means, for positively preventing fluid from entering said bottle until said cord is abruptly jerked, and
automatically closing valve means for sealing said bottle in response to said bottle being filled with fluid, whereby the fluid sample obtained in said bottle will not be contaminated by fluid from other levels as said sampling device is raised from said pool of fluid.
2. The device of claim 1 wherein said automatically closing valve means comprises
means defining a chamber communicating with said bottle through a first opening and communicating with the exterior of said device through a second opening, and
self-seating closure means in said chamber, having a specific gravity less than that of the fluid being sampled, for closing said second opening after said bottle is filled.
3. The device of claim 2 in which said remotely operable valve means comprises:
means for blocking said second opening and preventing fluid from entering said bottle through said chamber,
spring means biasing said means for blocking such that said second opening is normally closed, and
means for moving said means for blocking away from said second opening against the bias of said spring means and for holding said means for blocking away from said second opening after said cord is abruptly jerked.

4. The device of claim 2 wherein said self-seating closure means is a hollow metal sphere and said second opening is generally circular.

5. The device of claim 2 in which said first opening is threaded for engaging the threaded neck of a bottle.

6. A kit for taking liquid samples from a pool of liquid comprising:
- a plurality of sample bottles,
- a cord, and
- a sampling device attachable to said cord and lowerable thereby, said sampling device having
  - means for detachably engaging one of said plurality of sample bottles,
  - remotely operable valve means for keeping sealed positively the bottle which is engaged by said sampling device until said sampling device is properly positioned by means of said cord in said pool of liquid, and automatically closing valve means for sealing said bottle automatically in response to said bottle being filled with a liquid sample.

7. The kit of claim 6 further comprising a reel for said cord and a bobber attachable to said cord for indicating the depth to which said sampling device has been lowered.

8. The kit of claim 6 in which said remotely operable valve means is an inertia valve.

9. A sampling device for engaging a sample bottle, maintaining the bottle in a sealed condition as the bottle and the sampling device are lowered into a pool of fluid, permitting the bottle to fill with fluid and then sealing the bottle before it is removed from the pool of fluid comprising:
- annular housing means defining a cylindrical lower compartment for holding and protecting a sample bottle placed in said lower compartment,
- automatically closing valve means mounted in said housing means above said lower compartment defining a chamber and having a first opening which communicates with said sample bottle when said sample bottle is held in said lower compartment and having a second opening communicating with the exterior of the sampling device, said automatically closing valve means including a hollow metal sphere in said chamber for sealing said second opening when said bottle and said chamber are filled with fluid, and
- remotely operable valve means comprising:
  - a plunger slidably mounted on said housing and including a shaft having a detent,
  - a spring positioned to bias said plunger against said second opening to seal said second opening,
  - cord means attached to said plunger for moving said plunger away from said second opening when said remotely operable valve means is actuated, and
  - a spring biased pin for engaging said detent when said valve is actuated and for preventing said plunger from thereafter sealing said second opening.

* * * * *